United States Patent [19]

Press et al.

[11] Patent Number: 4,861,897

[45] Date of Patent: Aug. 29, 1989

[54] 2-ARYLOXYALKYLAMINOBENZOX-AZOLES AND 2-ARYLOXYALKYLAMINOBENZO-THIAZOLES

[75] Inventors: Jeffery B. Press, Rocky Hill; Pauline Sanfilippo, Flemington, both of N.J.

[73] Assignee: Ortho Pharmaceutical Corporation, Raritan, N.J.

[21] Appl. No.: 64,718

[22] Filed: Jun. 22, 1987

[51] Int. Cl.$^4$ ............................................. C07D 263/56
[52] U.S. Cl. .................................... 548/217; 544/368; 546/198; 548/179; 548/224
[58] Field of Search ..................... 548/179, 224, 217; 544/368; 546/198

[56] References Cited

U.S. PATENT DOCUMENTS 4,046,771  9/1977  Beecken ............................. 548/224

FOREIGN PATENT DOCUMENTS 1067151  5/1967  United Kingdom ................ 548/179

OTHER PUBLICATIONS

Cossey, J. Chem. Soc., 1965, p. 954.

*Primary Examiner*—Robert Gerstl
*Attorney, Agent, or Firm*—Benjamin F. Lambert

[57] ABSTRACT

The present invention relates to novel 2-aryloxyalkylaminobenzoxazoles and 2-aryloxyalkylaminobenzothiazoles. The novel compounds are useful as antisecretory agents.

7 Claims, No Drawings

2-ARYLOXYALKYLAMINOBENZOXAZOLES AND 2-ARYLOXYALKYLAMINOBENZOTHIAZOLES

BACKGROUND OF THE INVENTION

1. Field of the Invention

The present invention relates to novel 2-aryloxyalkylaminobenzoxazoles and 2-aryloxyalkylaminobenzothiazoles as described further below. The novel compounds are useful as antisecretory agents.

2. Description of the Prior Art

The prior art has described several benzoxazoles or benzothiazoles which are substituted at the 2-position by an aryloxyalkylamine group. Some of the compounds were said to have antidepressant activity and others demonstrated antimicrobial activity.

*J. Chem. Soc.* 954 (1965) describes compounds of the formula

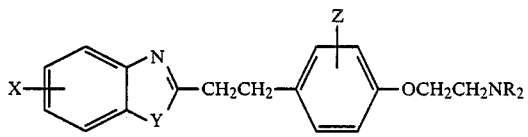

where X is halo or alkyl, Y is O or S, Z is halo or alkyl, and R is alkyl, which have antimicrobial activity.

*Arzneimittel. Forsch.* 16 (1), 33 (1966) discloses compounds of the formula

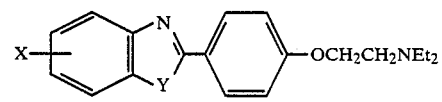

where X is halo or alkyl and Y is O or S, which also have antimicrobial activity.

These two references also describes compounds of the formula

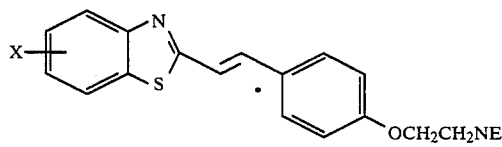

where X is halo or alkyl, which are antimicrobial agents.

None of these references disclose 2-aryloxyalkylaminobenzoxazoles and/or 2-aryloxyalkylaminobenzothiazoles which have antisecretory activity.

SUMMARY OF THE INVENTION

The present invention is directed to benzoxazole compounds or benzothiazole compounds of the formula

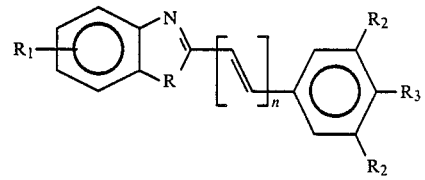

where
R may be O or S,
$R_1$ may be H, $C_1$-$C_4$ alkyl, $C_1$-$C_4$ alkoxy, Br, Cl or I,
$R_2$ and $R_3$ may be H or —O—$(CH_2)_m$—$NR_4R_5$, wherein one of $R_2$ and $R_3$ is H and the other is —O—$(CH_2)_m$—$NR_4R_5$, when $R_3$ is —O—$(CH_2)_m$—$NR_4R_5$, $R_2$ may independently be hydrogen, halogen, $C_1$-$C_4$ alkyl or $C_1$-$C_4$ alkoxy,
$R_4$ and $R_5$ may be the same or different, and may be $C_1$-$C_5$ alkyl, $C_3$-$C_6$ cycloalkyl, benzyl, benzyl substituted by $C_1$-$C_4$ alkyl, $C_1$-$C_4$ alkoxy, Br, Cl, I, or $R_4$ and $R_5$ together with N may be piperidine, pyrrolidine, imidazole or N-substituted piperazine, wherein the substituent may be $C_1$-$C_4$ alkyl, phenyl or phenyl substituted by $C_1$-$C_3$ alkoxy,
n may be 0 or 1, and
m may be 2-6,
with the provisos that when m is 2, $R_4$ and $R_5$ cannot both be $C_1$-$C_5$ alkyl and when m is 3, $R_4$ and $R_5$ cannot both be $C_1$-$C_2$ alkyl, and acid addition salts such as hydrochloride or hydrobromide.

The compounds of formula I are useful as antisecretory agents, such as antiulcer agents.

DETAILED DESCRIPTION OF THE INVENTION

The invention in its broadest aspects relates to benzoxazole compounds and benzothiazole compounds which have antisecretory activity. These compounds of the invention demonstrating an antisecretory activity are shown by formula I above. The benzoxazole compounds and benzothiazole compounds contain an aryloxyalkylamine substituent at the 2-position.

The preferred compounds of the invention are those wherein $R_2$ is H, n is 1, m is 2-5 and $R_4$ and $R_5$ are $C_1$-$C_5$ alkyl.

The compounds of formula I, wherein n is 1, can be prepared as shown in Scheme I.

SCHEME I

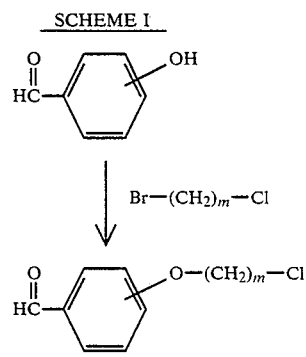

-continued
SCHEME I

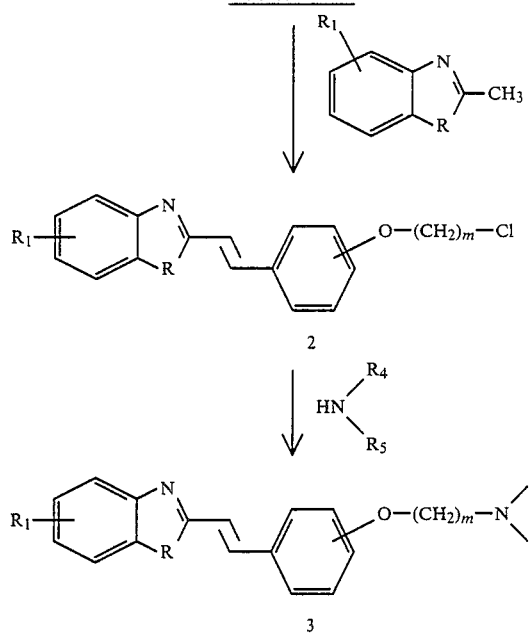

SCHEME II

Either m-hydroxybenzaldehyde or p-hydroxybenzaldehyde is treated with a 1-bromo-ω-chloroalkane in a solvent in the presence of a base for 12–48 hours at 20°–80° C. to produce the chloroalkoxy benzaldehyde 1. Chloroalkanes which can be utilized include 1-bromo-2-chloroethane, 1-bromo-3-chloropropane, 1-bromo-4-chlorobutane, 1-bromo-5-chloropentane or 1-bromo-6-chlorohexane. Suitable solvents include dimethylsulfoxide, dimethylformamide, tetrahydrofuran, diethylether, acetone or methanol. Sodium hydride, n-butyllithium, potassium hydroxide, potassium carbonate and the like can be used as the base. The chloroalkoxy benzaldehyde 1 is condensed with a benzoxazole or benzothiazole in a polar solvent in the presence of a base for 12–48 hours at 10°–50° C. to yield the 2-[2-(chloroalkoxyphenyl)ethenyl]benzoxazole or 2-[2-(chloroalkoxyphenyl)ethenyl]benzothiazole 2. Benzoxazoles or benzothiazoles which can be utilized include 2-methylbenzoxazole, 2-methylbenzothiazole, 2,5-dimethylbenzoxazole, 2,5-dimethylbenzothiazole, 5-chloro-2-methylbenzoxazole, 5-chloro-2-methylbenzothiazole, 6-methoxy-2-methylbenzoxazole or 6-methoxy-2-methylbenzothiazole. Suitable bases include sodium hydride, n-butyllithium or aqueous sodium hydroxide. Suitable solvents include dimethylsulfoxide, dimethylformamide or hexamethylphosphorous triamide.

The benzoxazole or benzothiazole 2 is reacted with an amine neat or in an inert solvent at 100°–150° C. for 4–72 hours to produce the aryloxyalkylamine benzoxazole or benzothiazole 3. Suitable inert solvents include benzene, toluene, 2-methoxyethylether or diglyme. Amines which can be utilized include dimethylamine, diethylamine, dipropylamine, dibutylamine, dipentylamine, piperidine, pyrrolidine, benzylamine, benzylmethylamine, N-methylpiperazine or 4-(2-methoxyphenyl)piperazine.

The compounds of formula I, wherein n is 0, can be prepared as shown in Scheme II.

Either m-hydroxybenzoic acid or p-hydroxybenzoic acid is treated with a 1-bromo-ω-chloroalkane in a solvent in the presence of a base for 12–48 hours at 10°–40° C. to produce the chloroalkoxybenzoic acid 4. Chloroalkanes which can be utilized include those discussed above in Scheme I. Suitable solvents include tetrahydrofuran, diethylether, dimethylformamide, methanol, ethanol or acetone. Sodium hydride, sodium hydroxide, potassium hydroxide, potassium carbonate and the like can be used as the base. The chloroalkoxybenzoic acid 4 is condensed with a 2-aminophenol or 2-aminothiophenol either in a melt or in a solvent at 180°–220° C. for 12–36 hours to yield the 2-(4-chloroalkoxyphenyl)benzoxazole or 2-(4-chloroalkoxyphenyl)benzothiazole 5. Suitable solvents include polyphosphoric acid, diethylaniline or dichlorobenzene. The benzoxazole or benzothiazole 5 is reacted with an amine in an inert solvent at 80°–150° C. for 12–72 hours. Suitable amines and inert solvents include those discussed above in Scheme I.

Pharmaceutical compositions containing a compound of the present invention as the active ingredient in intimate admixture with a pharmaceutical carrier can be prepared according to the conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 1 to about 100 mg/kg, and preferably from about 5 to about 25 mg/kg of the active ingredient.

The following examples describe the invention in greater particularity and are intended to be a way of illustrating but not limiting the invention.

EXAMPLE 1

(E)-2-[2-(3-Dibutylaminopropoxyphenyl)ethenyl]benzoxazole

To a suspension of sodium hydride (50% in oil, 3.9 g, 82 mmol) in tetrahydrofuran (100 ml) was added m-hydroxybenzaldehyde (5.0 g, 41 mmol). The mixture was stirred at room temperature under an atmosphere of nitrogen for one hour, then treated dropwise with 1-bromo-3-chloropropane (8.1 ml, 82 mmol). The mixture was stirred at room temperature for 48 hours, then quenched with methanol and filtered through Celite. The filtrate was concentrated, taken up in diethylether (300 ml), washed with water (2×100 ml) and dried over $Na_2SO_4$. The ether layer was concentrated to give 5.4 g (66% yield) of 3-chloropropoxybenzaldehyde as a yellow liquid. $^1H$ NMR (CDCl$_3$): δ 9.96 (s, 1H), 7.52–6.84 (m, 4H), 4.18 (t, J=5.1 Hz, 2H), 3.77 (t, J=5.1 Hz, 2H), 1.24 (m, 2H).

A solution of this product (5.0 g, 25 mmol) and 2-methylbenzoxazole (3.1 ml, 25 mmol) in dimethylsulfoxide (25 ml) was treated with 50% aqueous sodium hydroxide solution (10 ml). The solution was stirred at room temperature for 24 hours, diluted with water (500 ml) and extracted with methylene chloride (3×200 ml). The organic layer was dried over $Na_2SO_4$ and concentrated to give 4.0 g (51% yield) of (E)-2-[2-(3-chloropropoxyphenyl)ethenyl]benzoxazole (A) as an amber oil. $^1H$ NMR (CDCl$_3$): δ 7.89–6.88 (m, 10H), 4.11 (t, J=5.1 Hz, 2H), 3.59 (t, J=5.1 Hz, 2H), 1.09 (m, 2H).

A solution of this product (3.0 g, 9.3 mmol) in 40 ml dibutylamine was heated to 158° C. for ~21 hours. The excess dibutylamine was removed by distillation and the resulting oil was purified by flash chromatography (Si-Gel, 10% MeOH in CHCl$_3$) to produce 1.1 g (30% yield) of the free base of the title compound. The HCl salt was prepared by dropwise addition of concentrated hydrochloric acid to a solution of the free base in methanol, concentrated and recrystallized from acetone to give the salt of the title compound as an off-white solid, mp 136°–137° C. IR(KBr): 3400, 1600 cm$^{-1}$. MS: 406(M+). $^1H$ NMR (CDCl$_3$): δ 7.85–6.84 (m, 10H), 4.11 (t, J=5.2 Hz, 2H), 3.01–2.51 (m, 6H), 1.14–0.82 (m, 16H).

Theor. $C_{26}H_{34}N_2O_2.HCl.\frac{1}{2}H_2O$: C, 69.08; H, 8.03; N, 6.19. Found: C, 69.15; H, 8.51; N, 6.51.

EXAMPLE 2

(E)-2-[2-[3-[3-(4-Methylpiperazino)propoxy]phenyl]ethenyl]benzoxazole

The title compound was prepared as described in Example 1 starting with (A) of Example 1 (2.0 g, 6.4 mmol) and using N-methylpiperazine in place of dibutylamine to produce 0.56 g (25% yield of the free base of the title compound which was converted to the HCl salt, mp 250°–252° C. IR: 1600 cm$^{-1}$. MS: 378(MH+). $^1H$ NMR (CDCl$_3$): δ 7.82–7.00 (m, 10H), 4.13 (t, J=5.2 Hz, 2H), 3.31 (m, 13H), 2.41 (m, 2H).

Theor. $C_{23}H_{27}N_3O_2.2HCl$: C, 61.33; H, 6.49; N, 9.33. Found: C, 61.08; H, 6.47; N, 9.26.

EXAMPLE 3

(E)-2-[2-(3-Dipropylaminopropoxyphenyl)ethyenyl]benzoxazole

The procedure of Example 1 was followed starting with (A) of Example 1 (2.0 g, 6.4 mmol) and using dipropylamine in place of dibutylamine to produce 0.92 g (38% yield) of the free base of the named compound which was converted to the HCl salt, mp 167°–169° C. IR(KBr): 3400, 1600 cm$^{-1}$. MS: 379(MH+). $^1H$ NMR (CDCl$_3$): δ 7.91–7.01 (m, 10H), 4.15 (t, J=5.1 Hz, 2H), 3.08 (m, 6H), 2.32–0.79 (m, 12H).

Theor. $C_{24}H_{30}N_2O_2.2HCl.H_2O$: C, 61.40; H, 7.30; N, 5.97. Found: C, 61.44; H, 7.15; N, 5.65.

EXAMPLE 4

(E)-2-[2-(3-(1H-Imidazol-1-yl)propoxyphenyl)ethenyl]benzoxazole

The title compound was prepared by the procedure of Example 1 starting with (A) of Example 1 (8.0 g, 25 mmol) and using imidazole in place of dibutylamine to produce 2.1 g (24% yield) of the free base of the title compound which was converted to the HCl salt, mp 158°–159° C. IR(KBr): 3400, 1600 cm$^{-1}$. MS: 346(MH+). $^1H$ NMR (CD$_3$OD): δ 9.09 (s, 1H), 7.82–6.81 (m, 12H), 4.51 (t, J=5.4 Hz, 2H), 4.08 (t, J=5.1 Hz, 2H), 2.41 (m, 2H).

Theor. $C_{21}H_{19}N_3O_2.HCl.\frac{1}{2}H_2O$: C, 64.53; H, 5.42; N, 10.75. Found: C, 64.69; H, 5.05; N, 10.99.

EXAMPLE 5

(E)-2-[2-(3-Dipropylaminobutoxyphenyl)ethenyl]benzoxazole

To a suspension of sodium hydride (50% in oil, 3.9 g, 82 mmol), in tetrahydrofuran (100 ml) was added m-hydroxybenzaldehyde (5.0 g, 41 mmol). The mixture was stirred at room temperature under an atmosphere of nitrogen for ~2 hours, then treated with 1-bromo-4-chlorobutane (9.5 ml, 82 mmol) and allowed to stir at room temperature for ~2 days. The mixture was quenched with methanol, filtered through Celite and concentrated. The oil was dissolved in diethyl ether (300 ml), washed with water (2×100 ml) and dried over $Na_2SO_4$. The ether layer was concentrated to give 8.1 g (93% yield) of 3-chlorobutoxybenzaldehyde as a liquid. $^1H$ NMR (CDCl$_3$): δ 9.88 (s, 1H), 7.68–6.89 (m, 4H), 4.01 (t, J=5.2 Hz, 2H), 3.55 (t, J=5.4 Hz, 2 H), 1.89 (m, 4H).

A solution of this product (8.0, 38 mmol) and 2-methylbenzoxazole (4.6 ml, 38 mmol) in dimethylsulfoxide (40 ml) was treated with a 50% aqueous sodium hydroxide solution (25 ml). The mixture was stirred at room temperature for 24 hours, taken up in methylene chloride (500 ml), washed with water (3×200 ml) and dried over $Na_2SO_4$. The filtrate was concentrated to give 7.9 g (98% yield) of (E)-2-[2-(3-chlorobutoxyphenyl)ethenyl]benzoxazole (B) as an amber oil. $^1$H NMR ($CDCl_3$): δ 7.87–6.79 (m, 10H), 4.08 (t, J=5.1 Hz, 2H), 3.58 (t, J=5.4 Hz, 2H), 2.08–1.69 (m, 4H).

The title compound was prepared as described in Example 1 starting with (B) of this Example (3.0 g, 9.2 mmol) and using dipropylamine in place of dibutylamine to produce 0.61 g (17% yield) of the free base of the title compound which was converted to the HCl salt, mp 152°–153° C. IR(KBr): 1600 cm$^{-1}$. MS: 393(MH+). $^1$H NMR ($CDCl_3$): δ 8.24–6.97 (m, 10H), 4.08 (t, J=5.2 Hz, 2H), 3.18 (m, 6H), 1.98 (m, 8H), 0.99 (m, 6H).

Theor. $C_{25}H_{32}N_2O_2 \cdot 2HCl$: C, 64.51; H, 7.36; N, 6.02. Found: C, 64.22; H, 7.76; N, 5.78.

EXAMPLE 6

(E)-2-[2-(3-(1H-Imidazol-1-yl)butoxyphenyl)ethenyl]benzoxazole

The procedure of Example 1 was followed starting with (B) of Example 5 (8.0 g, 24 mmol) and using imidazole in place of dibutylamine to produce 0.91 g (11% yield) of the free base of the named compound which was converted to the HCl salt, mp 205°–207° C. IR(KBr): 3400, 1600 cm$^{-1}$. MS: 360(MH+). $^1$H NMR ($CD_3OD$): δ 9.01 (s, 1H), 7.98–6.99 (m, 12H), 4.39 (t, J=5.2 Hz, 2H), 4.09 (t, J=5.1 Hz, 2H), 2.00 (m, 4H).

Theor. $C_{22}H_{21}N_3O_2 \cdot HCl \cdot \frac{1}{2}H_2O$: C, 65.26; H, 5.72; N, 10.38. Found: C, 65.11; H, 5.67; N, 10.25.

EXAMPLE 7

(E)-2-[2-(3-(1H-Imidazol-1-yl)butoxyphenyl)ethenyl]-6-methoxybenzoxazole

The title compound was prepared according to Example 5 starting with 3-chlorobutoxybenzaldehyde of Example 5 (4.0 g, 19 mmol) and using 6-methoxy-2-methylbenzoxazole (3.0 g, 19 mmol) in place of 2-methylbenzoxazole to give 3.1 g (46% yield) of (E)-2-[2-(3-chlorobutoxyphenyl)ethenyl]-6-methoxybenzoxazole as an amber oil. $^1$H NMR ($CDCl_3$): δ 7.77–6.79 (m, 9H), 4.01 (t, J=5.3 Hz, 2H), 3.88 (s, 3H), 3.62 (m, 2H), 1.98 (m, 4H). Reaction of this product (2.5 g, 7.0 mmol) with imidazole produced 0.50 g (18% yield) of the free base of the title compound which was converted to the HCl salt, mp 208°–210° C. IR(KBr): 3400, 1600 cm$^{-1}$. MS: 390(MH+). $^1$H NMR ($CD_3OD$): δ 9.04 (s, 1H), 7.85–6.91 (m, 11H), 4.41 (t, J=5.3 Hz, 2H), 4.12 (t, J=5.1 Hz, 2H), 3.86 (s, 3H), 2.02 (m, 4H).

Theor. $C_{23}N_{23}N_3O_3 \cdot 2HCl \cdot \frac{1}{2}H_2O$: C, 58.60; H, 5.56; N, 8.91. Found: C, 58.45; H, 5.78; N, 9.18.

EXAMPLE 8

(E)-2-[2-(4-Dibutylaminopropoxyphenyl)ethenyl]benzoxazole

To a suspension of sodium hydride (50% in oil, 3.9 g, 82 mmol) in dimethylformamide (100 ml) was added p-hydroxybenzaldehyde (5.0 g, 41 mmol). The mixture was stirred at room temperature under an atmosphere of nitrogen for one hour, then treated dropwise with 1-bromo-3-chloropropane (8.1 ml, 82 mmol). The mixture was stirred at room temperature for 12 hours, quenched with methanol and filtered through Celite. The filtrate was dissolved in diethyl ether (500 ml), washed with water (3×200 ml) and dried over $Na_2SO_4$. The ether layer was concentrated to give 6.1 g (80% yield) of 4-chloropropoxybenzaldehyde as a yellow liquid. $^1$H NMR ($CDCl_3$): δ 9.95 (s, 1H), 7.85 (d, J=8.1 Hz, 2H), 7.01 (d, J=8.1 Hz, 2H), 4.21 (t, J=5 Hz, 2H), 3.81 (t, J=5 Hz, 2H), 1.26 (m, 2H).

To a solution of this product (5.0 g, 25 mmol) and 2-methylbenzoxazole (3.1 ml, 25 mmol) in dimethylsulfoxide (25 ml) was added a 50% aqueous sodium hydroxide solution (15 ml). The solution was stirred at room temperature for 24 hours, diluted with ice water (1 L), and the resulting precipitate was collected by filtration. The precipitate was washed with water and dried in vacuo to give (E)-2-[2-(4-chloropropoxyphenyl)ethenyl]benzoxazole (C) (6.4 g, 79% yield) as a yellow solid, mp 82°–83° C. IR(KBr): 1600 cm$^{-1}$. MS: 313(M+). $^1$H NMR ($CDCl_3$): δ 7.88–6.79 (m, 10H), 4.19 (t, J=5 Hz, 2H), 3.79 (t, J=5 Hz, 2H), 2.31 (m, 2H).

Theor. $C_{18}H_{16}NO_2Cl$: C, 68.90; H, 5.14; N, 4.46. Found: C, 69.20; H, 5.46; N, 4.27.

A solution of this product (6.0 g, 19 mmol) in 60 ml of dibutylamine was heated to 150° C. for 12 hours. The excess dibutylamine was removed by distillation and the resulting oil was purified by flash chromatography (Si-Gel, 9:1 $CHCl_3$-MeOH) to give 5.8 g (75% yield) of the free base of the title compound. The HCl salt was prepared by the addition of concentrated hydrochloric acid to a solution of the free base in methanol, concentrated, and recrystallized from acetone to give the HCl salt of the title compound as a yellow solid, mp 153°–154° C. IR(KBr): 3400, 1595 cm$^{-1}$. MS: 406(MH+). $^1$H NMR ($CDCl_3$): δ 7.99–6.81 (m, 10H), 4.15 (t, J=5 Hz, 2H), 3.09 (m, 6H), 2.44 (m, 2H), 1.99–0.87 (m, 16H).

Theor. $C_{26}H_{34}N_2O_2 \cdot HCl \cdot \frac{1}{2} H_2O$: C, 69.08; H, 8.03; N, 6.19. Found: C, 68.89; H, 7.92; N, 6.24.

EXAMPLE 9

(E)-2-[2-(4-Dipropylaminopropoxyphenyl)ethenyl]benzoxazole

The title compound was prepared as described in Example 8 starting with (C) of Example 8 (2.0 g, 6.4 mmol) and using dipropylamine in place of dibutylamine to produce 1.2 g (40% yield) of the title compound as the HCl salt, mp 172°–173° C. IR(KBr): 3400, 1600 cm$^{-1}$. MS: 379(MH+). $^1$H NMR ($CDCl_3$): δ 8.48–6.95 (m, 10H), 4.19 (t, J=5.1 Hz, 2H), 3.21 (m, 6H), 2.49–0.91 (m, 12H).

Theor. $C_{24}H_{30}N_2O_2 \cdot 2HCl \cdot H_2O$: C, 61.40; H, 7.29; N, 5.97. Found: C, 61.60; H, 7.16; N, 5.94

EXAMPLE 10

(E)-2-[2-(4-(1H-Imidazol-1-yl)propoxyphenyl)ethenyl]benzoxazole

The procedure of Example 8 was followed starting with (C) of Example 8 (2.0 g, 6.4 mmol) and using imidazole in place of dibutylamine to produce 1.4 g (63% yield) of the named compound as the HCl salt, mp 235°–236° C. IR(KBr): 3400, 1600 cm$^{-1}$. MS: 346(MH+). $^1$H NMR ($CD_3OD$): δ 9.04 (s, 1H), 7.99–6.81 (m, 12H), 4.72 (t, J=5.0 Hz, 2H), 4.11 (t, J=5.3 Hz, 2H), 2.34 (m, 2H).

Theor. $C_{21}H_{19}N_3O_2 \cdot HCl \cdot \frac{1}{2} H_2O$: C, 64.53; H, 5.42; N, 10.75 Found: C, 64.89; H, 5.48; N, 10.69.

EXAMPLE 11

(E)-2-[2-(4-Diethylaminopropoxyphenyl)ethenyl]benzoxazole

The title compound was prepared as described in Example 8 starting with (C) of Example 8 (2.0 g, 6.4 mmol) and using diethylamine in place of dibutylamine to produce 2.8 g (85% yield) diethylamine in place of dibutylamine to produce 2.8 g (85% yield) of the title compound as the HCl salt, mp 225°–226° C. IR(KBr): 1600 cm$^{-1}$. MS: 351(MH+). $^1$H NMR (CD$_3$OD): $\delta$ 7.99–6.81 (m, 10H), 4.24 (t, J=5.7 Hz, 2H), 3.09 (m, 6H), 2.44 (m, 2H), 0.87 (m, 6H).

Theor. C$_{22}$H$_{26}$N$_2$O$_2$.HCl: C, 68.29; H, 7.03; N, 7.24. Found: C, 68.34; H, 7.34; N, 6.91.

EXAMPLE 12

(E)-2-[2-[4-(3-Piperidinopropoxy)phenyl]ethenyl]benzoxazole

The procedure of Example 8 was followed starting with (C) of Example 8 (2.0 g, 6.4 mmol) and using piperidine in place of dibutylamine to produce 1.1 g, (41% yield) of the named compound as the HCl salt, mp 127°–128° C. IR(KBr): 3400, 1600 cm$^{-1}$. MS: 363(MH+). $^1$H NMR (CD$_3$OD): $\delta$ 7.89–6.81 (m, 10H), 4.24 (t, J=5.5 Hz, 2H), 2.65 (m, 6H), 1.75 (m, 8H).

Theor. C$_{23}$H$_{26}$N$_2$O$_2$.HCl.H$_2$O: C, 66.26; H, 6.77; N, 6.72. Found: C, 66.01; H, 6.92; N, 6.98.

EXAMPLE 13

(E)-2-[2-[4-(3-Methylbenzylaminopropoxy)phenyl]ethenyl]benzoxazole

The title compound was prepared in accordance with Example 8 starting with (C) of Example 8 (2.0 g, 6.4 mmol) and using methylbenzylamine in place of dibutylamine to produce 1.3 g (51% yield) of the title compound as the HCl salt, mp 194°–195° C. IR(KBr): 3400, 1600 cm$^{-1}$. MS: 398(M+). $^1$H NMR (CDCl$_3$): $\delta$ 7.74–6.69 (m, 15H), 3.99 (t, J=5.1 Hz, 2H), 2.91 (m, 3H), 2.41 (m, 2H), 1.94 (d, 3H).

Theor. C$_{26}$H$_{26}$N$_2$O$_2$.HCl.¼ H$_2$O: C, 71.06; H, 6.08; N, 6.37. Found: C, 71.16; H, 6.37; N, 6.35.

EXAMPLE 14

(E)-2-[2-[4-(2-Methoxyphenyl)piperazinopropoxyphenyl]ethenyl]benzoxazole

Following the procedure of Example 8, the named compound was prepared starting with (C) of Example 8 (2.0 g, 6.4 mmol) and using 1-(2-methoxyphenyl)piperazine in place of dibutylamine to produce 1.0 g (35% yield) of the named compound, mp 151°–152° C. IR(KBr): 3400, 1600 cm$^{-1}$. MS: 470(MH+). $^1$H NMR (CDCl$_3$): $\delta$ 7.89–6.79 (m, 14H), 4.09 (t, J=5.4 Hz, 2H), 3.83 (s, 3H), 3.11 (m, 4H), 2.68 (m, 6H), 2.04 (m, 2H).

Theor. C$_{29}$H$_{31}$N$_3$O$_3$.½ H$_2$O: C, 72.78; H, 6.74; N, 8.78. Found: C, 72.94; H, 6.59; N, 8.71.

EXAMPLE 15

(E)-2-[2-(4-Dibutylaminopropoxyphenyl)ethenyl]-5-methylbenzoxazole

The title compound was prepared as described in Example 8 starting with 4-chloropropoxybenzaldehyde of Example 8 (1.9 g, 10 mmol) and using 2,5-dimethylbenzoxazole (1.4 ml, 10 mmol) to give 2.2 g (68% yield) of (E)-2-[2-(4-chloropropoxyphenyl)ethenyl]-5-methylbenzoxazole as an amber oil. $^1$H NMR (CDCl$_3$): $\delta$ 7.19–6.84 (m, 10H), 4.21 (t, J=5.6 Hz, 2H), 3.23 (m, 2H), 2.52 (s, 3H), 2.44 (m, 2H).

Reaction of this product (2.2 g, 6.8 mmol) with dibutylamine produced 0.65 g (22% yield) of the title compound as the HCl salt, mp 143°–144° C. IR(KBr): 1600 cm$^{-1}$. MS: 421(MH+). $^1$H NMR (CDCl$_3$): $\delta$ 7.21–6.87 (m, 10H), 4.16 (t, J=5.6 Hz, 2H), 3.11 (m, 6H), 2.51 (s, 3H), 2.51–0.88 (m, 16H).

Theor. C$_{27}$H$_{36}$N$_2$O$_2$.2HCl: C, 65.71; H, 7.76; N, 5.68. Found: C, 65.63; H, 8.02; N, 5.58.

EXAMPLE 16

(E)-2-[2-(4-Dibutylaminopropoxyphenyl)ethenyl]-6-methoxybenzoxazole

The procedure of Example 8 was followed starting with 4-chloropropoxybenzaldehyde of Example 8 (1.9 g, 10 mmol) and using 6-methoxy-2-methylbenzoxazole in place of 2-methylbenzoxazole (1.6 ml, 10 mmol) to give 2.4 g (69% yield) of (E)-2-[2-(4-chloropropoxyphenyl)ethenyl]-6-methoxybenzoxazole as an amber oil. $^1$H NMR (CDCl$_3$): $\delta$ 8.29–6.99 (m, 9H), 4.22 (t, J=5.4 Hz, 2H), 3.93 (s, 3H), 3.24 (m, 2H), 2.51 (m, 2H).

Reaction of this product (2.4 g, 6.9 mmol) with dibutylamine produced 0.20 g (8% yield) of the named compound as the HCl salt, mp 151°–152° C. IR(KBr): 1600 cm$^{-1}$. MS: 437(MH+). $^1$H NMR (CDCl$_3$): $\delta$ 8.31–6.91 (m, 9H), 4.18 (t, J=5.1 Hz, 2H), 3.91 (s, 3H), 3.09 (m, 4H), 2.67–0.82 (m, 18H).

Theor. C$_{27}$H$_{36}$N$_2$O$_3$.2HCl: C, 63.65; H, 7.52; N, 5.50. Found: C, 63.93; H, 7.76; N, 5.45.

EXAMPLE 17

(E)-2-[2-(4-Dibutylaminoethoxyphenyl)ethenyl]benzoxazole

The title compound was prepared in accordance with Example 8, with p-hydroxybenzaldehyde (5.0 g, 41 mmol) and using 1-bromo-2-chloroethane (6.8 ml, 81 mmol) in place of 1-bromo-3-chloropropane to give 4.1 g (54% yield) of 4-chloroethoxybenzaldehyde as an amber oil. $^1$H NMR (CDCl$_3$): $\delta$ 9.88 (s, 1H), 7.81 (d, J=8.8 Hz, 2H), 7.00 (d, J=8.8 Hz, 2H), 4.31 (t, J=5.1 Hz, 2H), 3.87 (t, J=5.1 Hz, 2H).

Condensation of this product (4.0 g, 22 mmol) with 2-methylbenzoxazole (2.6 ml, 22 mmol) gave 2.1 g (33% yield) of (E)-2-[2-(4-chloroethoxyphenyl)ethenyl]benzoxazole as an off-white solid, mp 88°–90° C. $^1$H NMR (CDCl$_3$) $\delta$ 7.85–6.81 (m, 10H), 4.27 (t, J=5.1 Hz, 2H), 3.84 (t, J=5.1 Hz, 2H).

Reaction of this product (2.0 g, 6.7 mmol) with dibutylamine produced 2.3 g (80% yield) of the title compound as the HCl salt, mp 176°–177° C. IR(KBr): 1600 cm$^{-1}$. MS: 393(MH+). $^1$H NMR (CDCl$_3$): $\delta$ 7.84–6.84 (m, 10H), 4.62 (t, J=5.1 Hz, 2H), 3.50 (t, J=5.1 Hz, 2H), 3.12 (m, 4H), 2.01–1.97 (m, 14H).

Theor. C$_{25}$H$_{32}$N$_2$O$_2$.HCl: C, 69.99; H, 7.75; N, 6.53. Found: C, 70.15; H, 7.92; N, 6.49.

EXAMPLE 18

(E)-2-[2-(4-Dibutylaminobutoxyphenyl)ethenyl]benzoxazole

The procedure of Example 8 was followed with p-hydroxybenzaldehyde (5.0 g, 41 mmol) and using 1-bromo-4-chlorobutane (9.5 ml, 82 mmol) in place of 1-bromo-3-chloropropane to give 8.9 g (97% yield) of 4-chlorobutoxybenzaldehyde. $^1$H NMR (CDCl$_3$) $\delta$ 9.85 (s, 1H), 7.82 (d, J=8.1 Hz, 2H), 6.99 (d, J=8.1 Hz, 2H), 4.04 (t, J=5.3 Hz, 2H), 3.59 (t, J=5.3 Hz, 2H), 1.91 (m, 4H).

Condensation of this product (4.0 g, 19 mmol) with 2-methylbenzoxazole (2.3 ml, 19 mmol) gave (E)-2-[2-(4-chlorobutoxyphenyl)ethenyl]benzoxazole (D) (4.5 g, 72% yield) as an off-white solid, mp 92°–93° C. $^1$H NMR (CDCl$_3$): δ 7.88–6.81 (m, 10H), 4.08 (t, J=5.1 Hz, 2H), 3.34 (t, J=5.3 Hz, 2H), 2.55 (m, 4H).

Reaction of this product (3.0 g, 9.1 mmol) with dibutylamine produced the named compound (0.4 g, 11% yield) which was converted to the HCl salt, mp 172°–174° C. IR(KBr): 3400, 1600 cm$^{-1}$. MS: 421(MH+). $^1$H NMR (CD$_3$OD): δ 7.82–6.85 (m, 10H), 4.02 (t, J=5.2 Hz, 2H), 3.11 (m, 6H), 1.98–0.84 (m, 18H).

Theor. C$_{27}$H$_{36}$N$_2$O$_2$.HCl.H$_2$O: C, 68.26; H, 8.27; N, 5.6. Found: C, 68.31; H, 7.91; N, 5.48.

EXAMPLE 19

(E)-2-[2-(4-Piperidinobutoxyphenyl)ethenyl]benzoxazole

The title compound was prepared as described in Example 18 starting with (D) of Example 18 (2.5 g, 7.6 mmmol) and using piperidine in place of dibutylamine to produce 1.2 g (42% yield) of the title compound as the HCl salt, mp 230°–232° C. IR(KBr): 1600 cm$^{-1}$. MS: 377(MH+). $^1$H NMR (DMSO): δ 7.91–6.95 (m, 10H), 3.99 (t, J=5.2 Hz, 2H), 3.10 (m, 6H), 1.75 (m, 10H).

Theor. C$_{24}$H$_{28}$N$_2$O$_2$.HCl: C, 69.80; H, 7.08; N, 6.78. Found: C, 70.12; H, 7.09; N, 6.93.

EXAMPLE 20

(E)-2-[2-(4-Dipropylaminobutoxyphenyl)ethenyl]benzoxazole

The procedure of Example 18 was followed starting with (D) of Example 18 (2.5 g, 7.6 mmol) and using dipropylamine in place of dibutylamine to produce 0.90 g (30% yield) of the named compound as the HCl salt, mp 150°–152° C. IR(KBR): 1600 cm$^{-1}$. MS: 393(MH+). $^1$H NMR (CDCl$_3$): δ 8.09–6.87 (m, 10H), 4.01 (t, J=5.4 Hz, 2H), 3.02 (m, 6H), 1.95 (m, 8H), 0.99 (m, 6H).

Theor. C$_{25}$H$_{32}$N$_2$O$_2$.2HCl: C, 64.51; H, 7.36; N, 6.02. Found: C, 63.91; H, 7.33; N, 5.89.

EXAMPLE 21

(E)-2-[2-(4-(1H-Imidazol-1-yl)butoxyphenyl)ethenyl]-benzoxazole

The title compound was prepared in accordance with Example 18 starting with (D) of Example 18 (2.5 g, 7.6 mmol) and using imidazole in place of dibutylamine to produce 1.1 g (40% yield) of the title compound as the HCl salt, mp 204°–205° C. IR(KBr): 3400, 1600 cm$^{-1}$. MS: 360(MH+). $^1$H NMR (CD$_3$OD): δ 9.02 (s, 1H), 7.89–6.89 (m, 12H), 4.38 (t, J=5.3 Hz, 2H), 4.08 (t, J=5.4 Hz, 2H), 1.97 (m, 4H).

Theor. C$_{22}$H$_{21}$N$_3$O$_2$.HCl.H$_2$O: C, 63.84; H, 5.84; N, 10.15. Found: C, 63.60; H, 5.45; N, 9.87.

EXAMPLE 22

(E)-2-[2-(4-Diethylaminobutoxyphenyl)ethenyl]benzoxazole

The procedure of Example 18 was followed starting with (D) of Example 18 (2.5 g, 7.6 mmol) and using diethylamine in place of dibutylamine to produce 0.32 g (12% yield) of the named compound as the HCl salt, mp 219°–220° C. IR(KBr): 3400, 1600 cm$^{-1}$. MS: 365(MH+). $^1$H NMR (CDCl$_3$): δ 8.25–6.82 (m, 10H), 4.02 (t, J=5.4 Hz, 2H), 3.14 (m, 6H), 1.99 (m, 4H), 1.36 (m, 6H).

Theor. C$_{23}$H$_{28}$N$_2$O$_3$.HCl.H$_2$O: C, 65.94; H, 7.46; N, 6.69. Found: C, 66.12; H, 7.25; N, 6.57.

EXAMPLE 23

(E)-2-[2-(4-Pyrrolinobutoxyphenyl)ethenyl]benzoxazole

The title compound was prepared as described in Example 18 starting with (D) of Example 18 (3.0 g, 9.1 mmol) and using pyrrolidine in place of dibutylamine to produce 1.8 g (55% yield) of the title compound as the HCl salt, mp 229°–232° C. IR(KBr): 3400, 1600 cm$^{-1}$. MS: 363(MH+). $^1$H NMR (CD$_3$OD): δ 7.91–6.87 (m, 10H), 4.04 (t, J=5.2 Hz, 2H), 3.21 (m, 6H), 1.99 (m, 8H).

Theor. C$_{23}$H$_{26}$N$_2$O$_2$.HCl.H$_2$O: C, 65.25; H, 7.01; N, 6.72. Found: C, 65.48; H, 7.24; N, 6.99.

EXAMPLE 24

(E)-2-[2-(4-(1H-Imidazol-1-yl)pentoxyphenyl)ethenyl]-benzoxazole

The title compound was prepared in accordance with Example 8 from p-hydroxybenzaldehyde (5.0 g, 41 mmol) and using 1-bromo-5-chloropentane (11 ml, 82 mmol) in place of 1-bromo-3-chloropropane to give 9.4 g (87% yield) of 4-chloropentoxybenzaldehyde as a thick oil. $^1$H NMR (CDCl$_3$): δ 9.89 (s, 1c), 7.82 (d, J=8.7 Hz, 2H), 6.99 (d, J=8.7 Hz, 2H), 4.09 (t, J=5 Hz, 2H), 3.52 (t, J=5.1 Hz, 2H), 1.99–1.42 (m, 6H).

Condensation of this product (9.0 g, 40 mmol) and 2-methylbenzoxazole (4.8 ml, 40 mmol) gave (E)-2-[2-(4-chloropentoxyphenyl)ethenyl]benzoxazole (8.2 g, 60% yield) as an off-white solid, mp 92°–94° C. $^1$H NMR (CDCl$_3$): δ 7.85–6.81 (m, 10H), 4.02 (t, J=5.1 Hz, 2H), 3.51 (m, 2H), 1.99–1.41 (m, 6H).

Reaction of this product (3.0 g, 8.8 mmol) with imidazole produced the tital compound (1.2 g, 37% yield) which was converted to the HCl salt, mp 220°–222° C. IR(KBr): 3400, 1600 cm$^{-1}$. MS: 374(MH+). $^1$H NMR (CD$_3$OD): δ 9.00 (s, 1H), 7.99–6.85 (m, 12H), 4.31 (t, J=5.4 Hz, 2H), 4.08 (t, J=5.2 Hz, 2H), 2.11–1.45 (m, 6H).

Theor. C$_{23}$H$_{23}$N$_2$O$_2$.2HCl.½H$_2$O: C, 60.66; H, 5.75; N, 9.22. Found: C, 60.51; H, 5.68; N, 9.02.

EXAMPLE 25

(E)-2-[2-(3-Dibutylaminopropoxyphenyl)ethenyl]benzothiazole

The title compound was prepared as described in Example 1 starting with 3-chloropropoxybenzaldehyde (5.0 g, 25 mmol) and using 2-methylbenzothiazole (4.8 ml, 38 mmol) to give (E)-2-[2-(3-chloropropoxyphenyl)ethenyl]benzothiazole (6.1 g, 72% yield) as an amber oil. $^1$H NMR (CDCl$_3$): δ 8.04–6.89 (m, 10H), 4.01 (t, J=5.3 Hz, 2H), 3.52 (t, J=5.3 Hz, 2H), 1.99 (m, 4H).

Reaction of this product (3.0 g, 9.1 mmol) with dibutylamine produced 1.5 g (34% yield) of the title compound as the HCl salt, mp 182°–184° C. IR(KBr): 3400, 1600 cm$^{-1}$. MS: 422(M+). $^1$H NMR (CDCl$_3$): δ 8.28–6.87 (m 10H), 4.19 (t, J=5.3 Hz, 2H), 3.74–2.93 (m, 6H), 2.51–0.82 (m, 16H).

Theor. C$_{26}$H$_{34}$N$_2$OS.HCl.3/2H$_2$O: C, 64.24; H, 7.04; N, 5.76. Found: C, 64.17; H, 6.56; N, 5.27.

EXAMPLE 26

(E)-2-[2-(3-Dipropylaminobutoxyphenyl)ethenyl]benzothiazole

The named compound was prepared in accordance with Example 5 starting with 3-chlorobutoxybenzaldehyde (8.0 g, 38 mmol) and using 2-methylbenzothiazole (4.8 ml, 38 mmol) in place of 2-methylbenzoxazole to give 6.1 g (47% yield) of (E)-2-[2-(3-chlorobutoxyphenyl)ethenyl]benzothiazole (E) as an amber oil. $^1$H NMR (CDCl$_3$): δ 8.04–6.89 (m, 10H), 4.01 (t, J=5.1 Hz, 2H), 3.52 (t, J=5.1 Hz, 2H), 1.99 (m, 4H).

Reaction of the product (3.0 g, 8.7 mmol) with dipropylamine produced 1.3 g (37% yield) of the title compound as the HCl salt, mp 205°–207° C. IR(KBr): 1600 cm$^{-1}$. MS: 409(MH+). $^1$H NMR (CD$_3$OD): δ 8.02–6.89 (m, 10H), 4.01 (t, J=5.1 Hz, 2H), 3.11 (m, 6H), 1.82 (m, 4H), 0.89 (m, 6H).

Theor. C$_{25}$H$_{32}$N$_2$OS.2HCl: C, 62.32; H, 7.12; N, 5.82. Found: C, 62.65; H, 7.17; N, 5.88.

EXAMPLE 27

(E)-2-[2-(3-(1H-Imidazol-1-yl)butoxyphenyl)ethenyl]benzothiazole

The procedure of Example 26 was followed starting with (E) of Example 26 (3.0 g, 7.8 mmol) and using imidazole in place of dipropylamine to produce 0.52 g (16% yield) of the named compound as the HCl salt, mp 210°–211° C. IR(KBr): 3400, 1600 cm$^{-1}$. MS: 376(MH+). $^1$H NMR (CD$_3$OD): δ 8.91 (s, 1H), 8.00–6.87 (m, 12H), 4.22 (t, J=5.3 Hz, 2H), 3.95 (t, J=5.3 Hz, 2H), 1.84 (m, 4H).

Theor. C$_{22}$H$_{21}$N$_3$OS.2HCl.H$_2$O: C, 56.65; H, 5.40; N, 9.00. Found: C, 56.82; H, 5.25; N, 8.98.

EXAMPLE 28

(E)-2-[2-(4-Dibutylaminopropoxyphenyl)ethenyl]benzothiazole

The title compound was prepared in accordance with Example 8 starting with 4-chloropropoxybenzaldehyde (17.0 g, 86 mmol) and using 2-methylbenzothiazole (11 ml, 86 mmol) in place of 2-methylbenzoxazole to give 25.0 g (89% yield) of (E)-2-[2-(4-chloropropoxyphenyl)ethenyl]benzothiazole (F) as a yellow solid, mp 97°–99° C. $^1$H NMR (CDCl$_3$): δ 8.15–6.91 (m, 10H), 4.15 (t, J=5.2 Hz, 2H), 3.81 (t, J=5.2 Hz, 2H), 2.21 (m, 2H).

Reaction of this product (10.0 g, 30 mmol) with dibutylamine produced 8.4 g (66% yield) of the free base of the title compound which was converted to the HCl salt, mp 181°–182° C. IR(KBr): 3400, 1595 cm$^{-1}$. MS: 422(M+). $^1$H NMR (CDCl$_3$): δ 7.88–6.81 (m, 10H), 4.12 (t, J=5.3 Hz, 2H), 3.02–2.59 (m, 6H), 2.25–0.84 (m, 16H).

Theor. C$_{26}$H$_{34}$N$_2$OS.2HCl.2H$_2$O: C, 58.75; H, 7.58; N, 6.10. Found: C, 58.52; H, 7.14; N, 5.26.

EXAMPLE 29

(E)-2-[2-(4-Dipropylaminopropoxyphenyl)ethenyl]benzothiazole

The procedure of Example 28 was followed starting with (F) of Example 28 (5.0 g, 15 mmol) and using dipropylamine in place of dibutylamine to produce 3.4 g (57% yield) of the free base of the named compound which was converted to the HCl salt, mp 135°–137° C. IR(KBr): 3400, 1600 cm$^{-1}$. MS: 395(MH+). $^1$H NMR (CDCl$_3$): δ 8.15–7.00 (m, 10H), 4.11 (t, J=5.2 Hz, 2H), 3.08 (m, 6H), 2.58–0.75 (m, 12H).

Theor. C$_{24}$H$_{30}$N$_2$OS.2HCl.H$_2$O: C, 59.37; H, 7.06; N, 5.77. Found: C, 59.27; H, 6.96; N, 5.61.

EXAMPLE 30

(E)-2-[2-(4-Diethylaminopropoxyphenyl)ethenyl]benzothiazole

The title compound was prepared as described in Example 28 starting with (F) of Example 28 (3.0 g, 9.8 mmol) and using diethylamine in place of dibutylamine to produce 0.81 g (24% yield) of the title compound as the HCl salt, mp 187°–188° C. IR(KBr): 3400, 1600 cm$^{-1}$. MS: 367(MH+). $^1$H NMR (CD$_3$OD): δ 8.22–6.99 (m, 10H), 4.21 (t, J=5.1 Hz, 2H), 3.34 (m, 6H), 2.33 (m, 2H), 1.42 (m, 6H).

Theor. C$_{22}$H$_{26}$N$_2$OS.2HCl.½H$_2$O: C, 58.92; H, 6.52; N, 6.25. Found: C, 58.75; H, 6.39; N, 6.41.

EXAMPLE 31

(E)-2-[2-[4-(2-Methoxyphenyl)piperazinopropoxyphenyl]ethenyl]benzothiazole

The procedure of Example 28 was followed starting with (F) of Example 28 (0.6 g, 1.8 mmol) and using 1-(2-methoxyphenyl)piperazine in place of dibutylamine to produce 0.31 g (36% yield) of the named compound, mp 135°–137° C. IR(KBr): 3400, 1600 cm$^{-1}$. MS: 486(M+). $^1$H NMR (CDCl$_3$): δ 8.02–6.82 (m, 12H), 4.09 (t, J=5.2 Hz, 2H), 3.85 (s, 3H), 3.09 (m, 4H), 2.78 (m, 6H), 2.02 (m, 2H).

Theor. C$_{29}$H$_{31}$O$_2$S.½H$_2$O: C, 70.41; H, 6.31; N, 8.49. Found: C, 70.73; H, 6.04; N, 8.18.

EXAMPLE 32

(E)-2-[2-(4-(1H-Imidazol-1-yl)propoxyphenyl)ethenyl]benzothiazole

The title compound was prepared in accordance with Example 28 starting with (F) of Example 28 (5.0 g, 15 mmol) and using imidazole in place of dibutylamine to produce 2.4 g (39% yield) of the title compound as the HCl salt, mp 231°–232° C. IR(KBr): 1595 cm$^{-1}$. MS: 362(MH+). $^1$H NMR (CD$_3$OH): δ 9.01 (s, 1H), 7.99–6.91 (m, 12H), 4.21 (t, J=5.2 Hz, 2H), 4.03 (t, J=5.3 Hz, 2H), 2.32 (m, 2H).

Theor. C$_{21}$H$_{19}$N$_3$OS.2HCl: C, 58.07; H, 4.87; N, 9.67. Found: C, 57.76; H, 5.24; N, 9.61.

EXAMPLE 33

(E)-2-[2-(4-Piperidinopropoxyphenyl)ethenyl]benzothiazole

The procedure of Example 28 was followed starting with (F) of Example 28 (3.0 g, 9.8 mmol) and using piperidine in place of dibutylamine to produce 1.9 g (51% yield) of the free base of the named compound which was converted to the HCl salt, mp 215°–217° C. IR(KBr): 3400, 1595 cm$^{-1}$. MS: 379(MH+). $^1$H NMR (CD$_3$OD): δ 7.64–6.48 (m, 10H), 3.72 (t, J=5.2 Hz, 2H), 2.65 (m, 6H), 1.98 (m, 2H), 1.32 (m, 6H).

Theor. C$_{23}$H$_{26}$N$_2$OS.1HCl.3/2H$_2$O: C, 62.49; H, 6.84; N, 6.34. Found: C, 62.53; H, 6.94; N, 6.26.

EXAMPLE 34

(E)-2-[2-(4-Dibutylaminopropoxyphenyl)ethenyl]-5-methylbenzothiazole

The title compound was prepared as described in Example 28 starting with 4-chloropropoxybenzaldehyde (5.0 g, 25 mmol) and using 2,5-dimethylbenzothiazole (3.5 ml, 25 mmol) in place of 2-methylbenzothiazole to give (E)-2-[2-(4-chloropropoxyphenyl)ethenyl]benzothiazole (2.4 g, 30% yield) as an amber oil. $^1$H NMR (CDCl$_3$): δ 7.49–6.84 (m, 9H), 4.22 (t, J=5.2 Hz, 2H), 3.24 (t, J=5.3 Hz, 2H), 2.52 (s, 3H), 2.50 (m, 2H).

Reaction of this product (2.3 g, 6.9 mmol) with dibutylamine produced 1.2 g (40% yield) of the free base of the title compound which was converted to the HCl salt, mp 194°–195° C. IR(KBr): 1600 cm$^{-1}$. MS: 437(M+). $^1$H NMR (CDCl$_3$): δ 7.41–6.84 (m, 9H), 4.16 (t, J=5.2 Hz, 2H), 3.11 (m, 6H), 2.51 (s-1c), 2.50–0.88 (m, 16H).

Theor. C$_{27}$H$_{36}$N$_2$OS.2HCl: C, 63.64; H, 7.52; N, 5.50. Found: C, 63.47; H, 7.73; N, 5.39.

EXAMPLE 35

(E)-2-[2-(4-Dibutylaminopropoxyphenyl)ethenyl]-6-methoxybenzothiazole

The procedure of Example 28 was followed starting with 4-chloropropoxybenzaldehyde (5.0 g, 25 mmol) and using 6-methoxy-2-methylbenzothiazole (4.2 ml, 25 mmol) in place of 2-methylbenzothiazole to give (E)-2-[2-(4-chloropropoxyphenyl)ethenyl]-6-methoxybenzothiazole (2.5 g, 28% yield) as an amber oil. $^1$H NMR (CDCl$_3$): δ 7.44–6.82 (m, 9H9, 4.21 (t, J=5.3 Hz, 2H), 3.93 (s, 3H), 3.41 (t, J=5.3 Hz, 2H), 2.51 (m, 2H).

Reaction of this product (2.0 g, 5.6 mmol) with dibutylamine produced 1.3 g (52% yield) of the named compound as the HCl salt, mp 190°–200° C. IR(KBr); 1600 cm$^{-1}$. MS: 453(MH+). $^1$H NMR (CDCl$_3$): δ 7.41–6.88 (m, 9H), 4.13 (t, 2H), 3.91 (s, 3H), 3.09 (m, 6H), 2.41–0.88 (m, 16H).

Theor. C$_{27}$H$_{36}$N$_2$O$_2$S.2HCl.½H$_2$O: C, 60.66; H, 7.35; N, 5.24. Found: C, 60.74; H, 7.46; N, 5.17.

EXAMPLE 36

(E)-2-[2-(4-Dibutylaminopropoxyphenyl)ethenyl]-5-chlorobenzothiazole

The title compound was prepared in accordance with Example 28 starting with 4-chloropropoxybenzaldehyde (5.0 g, 25 mmol) and using 5-chloro-2-methylbenzothiazole (4.0 ml, 25 mmol) in place of 2-methylbenzothiazole to give (E)-2-[2-(4-chloropropoxyphenyl)ethenyl]-5-chlorobenzothiazole (2.9 g, 32% yield) as an amber oil. $^1$H NMR (CDCl$_3$): δ 7.88–6.91 (m, 9H), 4.17 (t, J=5.3 Hz, 3H), 3.34 (t, J=5.2 Hz, 2H), 2.54 (m, 2H).

Reaction of this product (2.5 g, 6.9 mmol) with dibutylamine produced 1.3 g (41% yield) of the title compound as the HCl salt, mp 176°–177° C. IR(KBr): 1600 cm$^{-1}$. MS: 458(MH+). $^1$H NMR (CDCl$_3$): δ 8.22–6.88 (m, 9H), 4.20 (t, J=5.3 Hz, 2H), 3.11 (m, 6H), 2.89–0.89 (m, 16H).

Theor. C$_{26}$H$_{33}$ClN$_2$O$_2$O$_2$S.2HCl: C, 58.92; H, 6.66; N, 5.29. Found: C, 58.74; H, 7.06; N, 5.20.

EXAMPLE 37

(E)-2-[2-(4-Dibutylaminoethoxyphenyl)ethenyl]benzothiazole

The named compound was prepared as described in Example 17 starting with 4-chloroethoxybenzaldehyde (4.0 g, 22 mmol) and using 2-methylbenzothiazole in place of 2-methylbenzoxazole to give (E)-2-[2-(4-chloroethoxyphenyl)ethenyl]benzothiazole (G) (7.6 g, 90% yield) as a yellow solid, mp 92°–94° C. $^1$H NMR (CDCl$_3$): δ 8.09–6.85 (m, 10H), 4.23 (t, J=5.2 Hz, 2H), 3.81 (t, J=5.2 Hz, 2H).

Reaction of this product (2.0 g, 6.3 mmol) with dibutylamine produced 1.1 g (36% yield) of the named compound as the HCl salt, mp 172°–173° C. IR(KBr): 3400, 1600 cm$^{-1}$. MS: 409(MH+). $^1$H NMR (CDCl$_3$): δ 8.37–6.79 (m, 10H), 4.67 (t, J=5.4 Hz, 2H), 3.55 (t, J=5.4 Hz, 2H), 3.12 (m, 4H), 1.99–0.79 (m, 14H).

Theor. C$_{25}$H$_{32}$N$_2$OS.2HCl.½H$_2$O: C, 61.21; H, 7.19; N, 5.71. Found: C, 61.37; H, 6.89; N, 5.64.

EXAMPLE 38

(E)-2-[2-(4-Dipropylaminobutoxyphenyl)ethenyl]benzothiazole

The procedure of Example 18 was followed starting with 4-chlorobutoxybenzaldehyde (10 g, 47 mmol) and using 2-methylbenzothiazole (6.0 ml, 47 mmol) in place of 2-methylbenzoxazole to give 10.1 g (63% yield) of (E)-2-[2-(4-chlorobutoxyphenyl)ethenyl]benzothiazole (H) as a solid, mp 98°–100° C. $^1$H NMR (CDCl$_3$): δ 8.01–6.89 (m, 10H), 4.01 (t, J=5.2 Hz, 2H), 3.61 (t, J=5.2 Hz, 2H), 1.94 (m, 4H).

Reaction of this product (5.0 g, 14.5 mmol) with dipropylamine produced 2.1 g (35% yield) of the named compound as the HCl salt, mp 155°–156° C. IR(KBr): 3400, 1600 cm$^{-1}$. MS: 409(MH+). $^1$H NMR (CD$_3$OD): δ 8.19–6.99 (m, 10H), 4.10 (t, J=5.2 Hz, 2H), 3.12 (m, 6H), 1.85 (m, 8H), 1.02 (m, 6H).

Theor. C$_{25}$N$_{32}$N$_2$OS.HCl.½H$_2$O: C, 66.13; H, 7.55; N, 6.17. Found: C, 66.20; H, 7.66; N, 6.18.

EXAMPLE 39

(E)-2-[2-(4-1H-Imidazol-1-yl)ethoxyphenyl)ethenyl]benzothiazole

The title compound was prepared in accordance with Example 37 starting with (G) of Example 37 (2.5 g, 7.9 mmol) and using imidazole in place of dibutylamine to produce 1.1 g (31% yield) of the title compound as the HCl salt, mp 226°–227° C. IR(KBr): 1595 cm$^{-1}$. MS: 348(MH+). $^1$H NMR (CD$_3$OD): δ9.13 (s, 1H), 8.09–6.91 (m, 12H), 4.74 (t, J=5.3 Hz, 2H), 4.47 (t, J=5.3 Hz, 2H).

Theor. C$_{20}$H$_{17}$N$_3$OS.3HCl: C, 52.59; H, 4.41; N, 9.19. Found: C, 53.06; H, 4.32; N, 9.04.

EXAMPLE 40

(E)-2-[2-(4-(1H-Imidazol-1-yl)butoxyphenyl)ethenyl]benzothiazole

The named compound was prepared as described in Example 38 starting with (H) of Example 38 (3.0 g, 8.7 mmol) and using imidazole in place of dipropylamine to produce 1.5 g (46% yield) of the named compound as the HCl salt, mp 214°–217° C. IR(KBr): 3400, 1595 cm$^{-1}$. MS: 376(MH+). $^1$H NMR (CD$_3$OD): δ 9.01 (s, 1H), 7.88–6.91 (m, 12H), 4.21 (t, J=5.2 Hz, 2H), 3.34 (t, J=5.2 Hz, 2H), 2.25 (m, 4H).

Theor. C$_{22}$H$_{21}$N$_3$OS.HCl.H$_2$O: C, 61.45; H, 5.39; N, 9.77. Found: C, 60.95; H, 5.22; N, 9.56.

EXAMPLE 41

(E)-2-[2-(4-Diethylaminobutoxyphenyl)ethenyl]benzothiazole

The procedure of Example 38 was followed starting with (H) of Example 38 (3.0 g, 8.7 mmol) and using diethylamine in place of dipropylamine to produce 1.2 g (31% yield) of the title compound as the HCl salt, mp 205°–207° C. IR(KBr): 3400, 1605 cm$^{-1}$. MS: 381(MH+). $^1$H NMR (CD$_3$OD): δ 8.14–7.04 (m, 10H), 4.14 (t, J=5.2 Hz, 2H), 3.25 (m, 6H), 1.98 (m, 4H), 1.34 (m, 6H).

Theor. C$_{23}$H$_{28}$N$_2$OS.2HCl.2H$_2$O: C, 56.43; H, 7.00; N, 5.12. Found: C, 56.33; H, 6.68; N, 5.70.

EXAMPLE 42

(E)-2-[2-(4-Pyrrolidinobutoxyphenyl)ethenyl]benzothiazole

The title compound was prepared in accordance with Example 38 starting with (H) of Example 38 (3.0 g, 8.7 mmol) and using pyrrolidine in place of dipropylamine to produce 1.1 g (33% yield) of the title compound as the HCl salt, mp 220°–222° C. IR(KBr): 3410, 1600 cm$^{-1}$. MS: 379(MH+). $^1$H NMR (CD$_3$OD): δ 8.02–6.91 (m, 10H), 4.12 (t, J=5.2 Hz, 2H), 3.23 (m, 6H), 2.54 (m, 4H), 2.21 (m, 4H).

Theor. C$_{23}$H$_{26}$N$_2$OS.HCl.½ H$_2$O: C, 65.15; H, 6.66; N, 6.60. Found: C, 64.76; H, 6.61; N, 6.54.

EXAMPLE 43

2-(4-Dibutylaminopropoxyphenyl)benzothiazole

To a suspension of sodium hydride (50%, 8.0 g, 164 mmol) in dimethylformamide (200 ml) was added p-hydroxybenzoic acid (10.0 g, 82 mmol) portionwise. The mixture was stirred at room temperature for two hours, treated with 1-chloro-3-bromopropane (16 ml, 164 mmol) and allowed to stir at room temperature for 48 hours. The mixture was quenched with methanol, acidified with concentrated hydrochloric acid and filtered through Celite. The filtrate was diluted with diethyl ether (500 ml), washed with water (3×200 ml) and dried over Na$_2$SO$_4$. The ether solution was concentrated to give 4-chloropropoxybenzoic acid (1.1 g, 6% yield) as an off-white solid, mp 136°–138° C. $^1$H NMR (DMSO): δ 12.00 (s, 1H), 7.88 (d, J=8.8 Hz, 2H), 7.01 (d, J=8.8 Hz, 2H), 4.24 (t, J=5.0 Hz, 2H), 3.54 (t, J=5.1 Hz, 2H), 2.23 (m, 2H).

A solution of this product (10.0 g, 47 mmol) in tetrahydrofuran (50 ml) was treated with oxalyl chloride (4 ml, 47 mmol) and heated to 50° C. for two hours. The solution was concentrated, tetrahydrofuran (20 ml) was added, and then 2-aminothiophenol (5.0 ml, 47 mmol). The solution was stirred at room temperature until a semi-solid formed (~72 hours). The solid was isolated by filtration and recrystallized from methylene chloride-hexanes to give 2-(4-chloropropoxyphenyl)benzothiazole (I) (5.7 g, 36% yield) as an off-white solid, mp 141°–143° C. $^1$H NMR (CDCl$_3$): δ 8.21–6.72 (m, 8H), 4.19 (t, J=5.1 Hz, 2H), 3.68 (m, 2H), 2.21 (m, 2H).

Reaction of this product (1.0 g, 3.1 mmol) with dibutylamine produced 0.42 g (35% yield) of the title compound as the HCl salt, mp 136°–137° C. IR(KBr): 3400, 1600 cm$^{-1}$. MS: 379(M+). $^1$H NMR (CDCl$_3$): δ 8.42–6.85 (m, 8H), 4.21 (t, J=5.1 Hz, 2H), 3.12 (m, 6H), 1.99–0.85 (m, 16H).

Theor. C$_{24}$H$_{32}$N$_2$OS.2HCl.½ H$_2$O: C, 60.24; H, 7.37; N, 5.85. Found: C, 59.99; H, 7.29; N, 5.69.

EXAMPLE 44

2-(4-Dipropylaminopropoxyphenyl)benzothiazole

The title compound was prepared as described in Example 43 starting with (I) of Example 43 (2.0 g, 6.3 mmol) and using dipropylamine in place of dibutylamine to produce 0.41 g (19% yield) of the title compound as the HCl salt, mp 142°–143° C. IR(KBr): 3400, 1600 cm$^{-1}$. MS: 369(MH+). $^1$H NMR (CDCl$_3$): δ 8.19–6.95 (m, 8H), 4.19 (t, J=5.1 Hz, 2H), 3.01 (m, 6H), 2.64–0.82 (m, 12H).

Theor. C$_{22}$H$_{28}$N$_2$OS.2HCl.½ H$_2$O: C, 58.65; H, 6.94; N, 6.22. Found: C, 58.55; H, 6.85; N, 6.17.

EXAMPLE 45

(E)-2-[2-(3-Chloro-4-dipropylaminobutoxyphenyl)ethenyl]benzoxazole

The title compound was prepared as in Example 8 starting with 3-chloro-4-hydroxybenzaldehyde (10 g, 55 mmol) and 1-bromo-4-chlorobutane (8.4 ml, 82 mmol) to give 15.9 (95% yield) of 3-chloro-4-chlorobutoxybenzaldehyde as an oil. $^1$H NMR (CDCl$_3$): δ 9.81 (s, 1H), 7.51 (m, 4H), 3.91 (t, 2H), 3.62 (t, 2H), 2.09 (m, 4H).

A solution of this product (8.0 g, 35 mmol) and 2-methylbenzoxazole (4.5 ml, 35 mmol) was reacted as in Example 8 to give 9.7 g (74% yield) of (E)-2-[2-[(3-chloro)-4-chlorobutoxyphenyl]ethenyl]benzoxazole. $^1$H NMR (CDCl$_3$): δ 7.83–6.87 (m, 8H), 4.03 (t, 2H), 3.57 (t, 2H), 2.11 (m, 4H). A solution of this product (3.0 g, 8.4 mmol) in dipropylamine (20 ml) was reacted as in Example 8 to give 600 mg (20% yield) of the free base of the title compound which was converted to the HCl salt, mp 192°–194° C. IR(KBr): 1596 cm$^{-1}$. MS: 427(MH+). $^1$H NMR (CD$_3$OD): δ 8.01–6.91 (m, 8H), 4.08 (t, 2H), 2.52 (m, 6H), 2.01–1.12 (m, 14H).

Theor. C$_{25}$H$_{31}$N$_2$OCl.HCl: C, 64.79; H, 6.96; N, 6.04. Found: C, 64.47; H, 6.66; N, 5.83.

EXAMPLE 46

(E)-2-[2-(3,5-Dimethoxy-4-dipropylaminopropoxyphenyl)ethenyl]benzoxazole

The title compound was prepared as in Example 8 starting with 4-hydroxy-3,5-dimethoxybenzaldehyde (10 g, 55 mmol) and 1-bromo-3-chloropropane (8.4 ml, 82 mmol) to give 16.1 g (95% yield) of 4-chloropropoxy-3,5-dimethoxybenzaldehyde as an amber oil. $^1$H NMR (CDCl$_3$): δ 9.81 (s, 1H), 7.51 (s, 2H), 3.91 (t, 2H), 3.62 (t, 2H), 3.21 (s, 6H), 2.00 (m, 2H).

A solution of this product (8.0 g, 35 mmol) and 2-methylbenzoxazole (4.5 ml, 35 mmol) was reacted as in Example 8 to give 10.3 g (78% yield) of (E)-2-[2-[(4-chloropropoxy)-3,5-dimethoxyphenyl]ethenyl]benzoxazole. $^1$H NMR (CDCl$_3$): δ 7.81–6.88 (m, 8H), 4.01 (t, 2H), 3.66 (t, 2H), 3.31 (s, 6H), 2.00 (m, 2H). A solution of this product (3.0 g, 8.4 mmol) is dipropylamine (20 ml) was reacted as in Example 8 to give 340 mg (13% yield) of the free base of the title compound which was converted to the HCl salt, mp 117°–120° C. IR(KBr): 1625, 1496 cm$^{-1}$. MS: 439(MH+). $^1$H NMR (CD$_3$OD): δ 7.99–6.91 (m, 8H), 4.11 (t, 2H), 3.44 (m, 6H), 2.39 (s, 6H), 2.50 (m, 4H), 2.01–1.22 (m, 8H).

Theor. C$_{26}$H$_{34}$N$_2$O$_4$.HCl.½ H$_2$O: C, 64.52; H,, 7.50; N, 5.79. Found: C, 64.54; H, 7.78; N, 5.73.

EXAMPLE 47

(E)-2-[2-(3,5-Dimethoxy-4-dipropylaminopropoxyphenyl)ethenyl]benzoxazole

The procedure of Example 8 was followed starting with 4-hydroxy-3,5-dimethylbenzaldehyde (10 g, 66 mmol) and 1-bromo-3-chloropropane (11 ml, 100 mmol) to give 16.1 g (95% yield) of 4-chloroproxy-3,5-dimethylbenzaldehyde as an amber oil. $^1$H NMR (CDCl$_3$): δ 9.81 (s, 1H), 7.51 (s, 2H), 8.91 (t, 2H), 3.62 (t, 2H), 2.34 (s, 6H), 2.00 (m, 2H).

To a solution of this product (8.0 g, 35 mmol) and 2-methylbenzoxazole (4.5 ml, 35 mmol) in DMSO (35 ml) was added a 50% aqueous sodium hydroxide solution (15 ml) and worked up as in Example 8 to give (E)-2-[2-(3,5-dimethyl)-4-chloropropoxyphenyl)ethenyl]benzoxazole as a solid (8.2 g, 70% yield). $^1$H NMR (CDCl$_3$): δ 7.81–6.88 (m, 8H), 4.01 (t, 2H), 3.66 (t, 2H), 2.31 (s, 6H), 2.00 (m, 2H).

A solution of this product (3.0 g, 8.4 mmol) in 20 ml of dipropylamine was reacted as in Example 8 to give 1.1 g (31% yield) of the free base of the title compound which was converted to the HCl salt as a yellow solid, mp 162°–165° C. IR(KBr): 1626, 1567 cm$^{-1}$. MS: 407(MH+). $^1$H NMR (CD$_3$OD): δ 7.99–6.91 (m, 8H), 4.11 (t, 2H), 3.44 (m, 6H), 2.50 (m, 2H), 2.39 (s, 6H), 2.01–1.22 (m, 10H).

Theor. C$_{26}$H$_{34}$N$_2$O$_2$.HCl.H$_2$O: C, 67.73; H, 8.09; N, 6.08. Found: C, 67.44; H, 8.21; N, 5.82.

By substituting 2-aminophenol, 2-amino-4-chlorophenol or 2-amino-4-methylphenol for the 2-aminothiophenol of Example 43, the corresponding benzoxazole, 5-chlorobenzoxazole and 5-methylbenzoxazole compounds are obtained.

By substituting 1-bromo-ω-chloroalkane disclosed in Examples 1–42 for the 1-bromo-3-chloropropane of Example 43, the corresponding aminoalkoxy derivatives are obtained. By substituting the amines disclosed in Examples 1–42 for the dibutylamine of Example 43, the corresponding aminoalkoxy derivatives are obtained. Additional aminoalkoxy benzoxazoles or benzothiazoles are produced in accordance with any of the preceding examples by using the following amines in place of the amines utilized in the preceding examples to treat the chloroalkoxyphenylthiazoles: dibenzylamine, cyclohexylamine, dicyclohexylamine, propylamine, cyclopropylamine, N-methylbutylamine, N-methylcyclohexylamine, 4-methylbenzylamine, 4-methoxybenzylamine and 4-chlorobenzylamine.

ANTISECRETORY ACTIVITY

Gastro-duodenal ulcerations are produced and maintained by excess secretion of gastric acid. The predominant source of this acid is found in the parietal cells whose exocrine secretion in the stomach is almost pure hydrochloric acid (*Am. J. Gastro.* 77, 281 (1982)). The parietal cells are stimulated to secrete acid by such substances as gastrin, acetylcholine and histamine, (*Drugs*, 26, 439 (1983)). Inhibition of parietal cell secretion via an antihistamine, anticolinergic, anti-gastrin or via inhibition of internal mechanisms of the parietal cells either singularly or in combination provides a useful treatment for ulcers.

The anti-secretory activity of representative compounds was examined by employing three different assays, as more fully described in Examples 45–47.

EXAMPLE 48

Isolated Parietal Cell Assay

The isolated parietal cell assay was conducted using the procedures of Batzri, S. et al., *Biochemica et Biophysica Acta* 508, 328 (1978) and Soll, A. H. *Am. J. Physiol.* 238, G366 (1980). Basically, parietal cells were isolated from the fundic mucosa of rabbit stomachs by a four-stage collagenase digestion process. The supernatant fractions from the last two stages of this process contain the individual parietal cells. This cell suspension was centrifuged and reconstituted in a modified Hank's buffer to contain 1–2×10$^6$ cells/ml. The cells in this suspension were then evaluated for their ability to accumulate $^{14}$C-aminopyrine ($^{14}$C-AP), a weak base which has been shown to accumulate in acidic environments such as the parietal cell. This accumulation was stimulated by histamine and was blocked by H$_2$ antagonists. The cells were incubated with 0.4–0.5×10$^6$ cpm $^{14}$C-AP, with various concentrations of histamine as a stimulant, 1×10$^{-5}$M isobutylmethylxanthine, and the test compound added in a 20 μl volume of buffer or DMSO. The flasks were incubated in a shaking water bath at 37° C. for 20 minutes. Two aliquots were then taken from each flask and cell pellets were collected by centrifugation. The pellets were solubilized with Protosol (New England Nuclear) and radioactivity determined by liquid scintillation spectrometry. Data is presented as the IC$_{50}$ vhist, the concentration of compound required to inhibit $^{14}$C-AP accumulation in the histamine stimulated parietal cell by 50%. When dibutyryl cAMP was used to stimulate the cells instead of histamine, a similar inhibition of $^{14}$C-AP accumulation was measured and the data are presented as the IC$_{50}$ vcAMP, the concentration required to inhibit $^{14}$C-AP accumulation in the cAMP stimulated parietal cells by 50%. The results are shown in Table I.

EXAMPLE 49

Inhibition of Parietal Cell H+K+ATPase

The inhibition of parietal cell H+K+ATPase was determined in fundic mucosa from New Zealand white rabbits which were homogenized in a modified Tris buffer consisting of 250 mM sucrose, 0.2 mM EDTA and 5.0 mM Tris adjusted to pH 7.4 with HCl. The activity was measured in a 1 ml incubation volume containing 50 mM Tris pH 7.4, 2 mM MgCl$_2$, 2 mM Na$_2$ATP, with or without 20 mM KCl and vehicle control (dimethylsulfoxide) or test compound added in a 0.02 ml volume. Typically, 20–50 μg membrane protein was added and the tubes were preincubated with test compound for 10 minutes at 37° C. Substrate, Na$_2$ATP, was then added and the tubes were incubated for another 15 minutes at 37° C. The reaction was stopped by the addition of 1 ml 14% trichloroacetic acid and the samples were centrifuged at 2,000 xg for 10 minutes. The amount of inorganic phosphate present in an aliquot of supernatant was determined. H+K+ATPase activity was determined after correcting for the basal (Mg++ only) enzyme activity present in the membrane preparation. The amount of inhibition of the ATPase is shown in Table I.

EXAMPLE 50

Gastric Secretion

The inhibitory activity of the compounds on acid output was tested using pylorus ligation in a modification of the procedure of Shay, H. et al., *Gastroenterology* 26, 906 (1954). Basically, male Charles River Sprague Dawley derived rats weighing 150–300 grams were deprived of food but not water for 18–24 hours prior to use. Water was withheld during the experiment, however. The rats were weighed, anesthetized with ether and the pylorus ligated according to the method of Shay et al., supra. Treatment or vehicle control was then administered intraduodenally (i.d.) or subcutaneously (s.c.). Rats were housed two/cage and sacrificed with CO$_2$ four hours after ligation. The stomachs were removed, rinsed, and contents emptied into a graduated centrifuge tube. The tubes were centrifuged, the volume of gastric juice recorded, and any samples obviously contaminated by feces, food or blood were eliminated. A 1 ml aliquot of gastric juice was titrated with 0.1N NaOH to a pH of 7.0-7.4. The volume of gastric juice secreted, the acid concentration, and the product of the volume times the concentration, i.e., the total amount of acid secreted, were measured. The amount of the acid output by the test compounds compared to the control is shown in Table I.

TABLE I

| Compound (Example) | Example 48 IC$_{50}$(μM) | Example 49 % Inhibition at Concentration | Example 50 % Acid Secreted at mpK |
|---|---|---|---|
| 1 | .27 vhist; .14 vcAMP | 49% @ 10$^{-4}$ M | -78% @ 20<br>-52% @ 10<br>-44% @ 5 |
| 2 | 1.2 vhist; .41 vcAMP | 50% @ 94 μM | -9% @ 20 |
| 3 | .20 vhist; .24 vcAMP | 50% @ 29 μM | -49% @ 20 |
| 4 | .21 vhist; .34 vcAMP | 50% @ 10 μM | -38% @ 20 |
| 5 | .12 vhist; .31 vcAMP | 50% @ 14 μM | -74% @ 20<br>-25% @ 10 |
| 6 | .28 vhist; .23 vcAMP | 50% @ 13 μM | -45% @ 20 |
| 7 | .12 vhist; .18 vcAMP | 50% @ 74 μM | — |
| 8 | .15 vhist; .15 vcAMP | 17% @ 10$^{-4}$ M | -96% @ 40<br>-44% @ 10 |
| 9 | .22 vhist; .35 vcAMP | 50% @ 25 μM | -97% @ 40<br>-77% @ 20<br>-29% @ 10 |
| 10 | .29 vhist; .25 vcAMP | 50% @ 64 μM | -26% @ 20 |
| 11 | .32 vhist; .98 vcAMP | 20% @ 10$^{-4}$ M | -54% @ 40 |
| 12 | .26 vhist; .15 vcAMP | 50% @ 27 μM | -88% @ 40 |
| 13 | .41 vhist; 1.4 vcAMP | 50% @ 66 μM | -34% @ 20 |
| 14 | .6 vhist; .8 vcAMP | 43% @ 10$^{-4}$ M | -8% @ 20 |
| 15 | .26 vhist; .34 vcAMP | 50% @ 27 μM | -88% @ 40 |
| 16 | .08 vhist; .05 vcAMP | 50% @ 26 μM | -64% @ 40 |
| 17 | .26 vhist; .54 vcAMP | 43% @ 10$^{-4}$ M | -43% @ 20 |
| 18 | .18 vhist; <10 vcAMP | 50% @ 20 μM | -14% @ 10 |
| 19 | .17 vhist; .33 vcAMP | 50% @ 40 μM | -42 @ 20 |
| 20 | .39 vhist; .11 vcAMP | 50% @ 21 μM | -90% @ 20<br>-59% @ 10 |
| 21 | .27 vhist; .33 vcAMP | 50% @ 30 μM | -14% @ 20 |
| 22 | .08 vhist; .12 vcAMP | 50% @ 74 μM | -31% @ 20 |
| 23 | .17 vhist; .24 vcAMP | 50% @ 84 μM | -24% @ 40 |
| 24 | .28 vhist; .23 vcAMP | 50% @ 13 μM | -45% @ 20 |
| 25 | .20 vhist; .33 vcAMP | 61% @ 10$^{-4}$ M | -40% @ 20 |
| 26 | .09 vhist; .18 vcAMP | 50% @ 19 μM | -80% @ 40<br>-42% @ 20 |
| 27 | .11 vhist; .21 vcAMP | 50% @ 4.7 μM | -83% @ 40<br>-42% @ 20 |
| 28 | 21 vhist; .45 vcAMP | 46% @ 10$^{-4}$ M | -49% @ 20<br>-25% @ 10 |
| 29 | .26 vhist; .21 vcAMP | — | -30% @ 20 |
| 30 | .37 vhist; .15 vcAMP | — | -71% @ 40 |
| 31 | 1.7 vhist; 3.4 vcAMP | 33% @ 10$^{-4}$ M | -11% @ 20 |
| 32 | .13 vhist; .34 vcAMP | — | -22% @ 20 |
| 34 | .29 vhist; .53 vcAMP | 52% @ 10$^{-4}$ M | -14% @ 20 |
| 35 | .26 vhist; .46 vcAMP | 50% @ 60 μM | -31% @ 20 |
| 36 | .40 vhist; .5 vcAMP | 52% @ 10$^{-4}$ M | -26% @ 40 |
| 37 | .43 vhist; .60 vcAMP | 43% @ 10$^{-4}$ M | -14% @ 20 |
| 38 | .03 vhist; .12 vcAMP | 50% @ 21 μM | -93% @ 40 |
| 39 | .39 vhist; .46 vcAMP | 19% @ 10$^{-4}$ M | -32% @ 40 |
| 40 | .20 vhist; .26 vcAMP | — | -17% @ 40 |
| 41 | .18 vhist; .35 vcAMP | 50% @ 44 μM | -52% @ 20 |
| 42 | .16 vhist; .26 vcAMP | 50% @ 17 μM | -20% @ 40 |
| 43 | .25 vhist; 2.6 vcAMP | 50% @ 18 μM | — |
| 44 | .21 vhist; .14 vcAMP | 67% @ 10$^{-4}$ M | -42% @ 20 |
| 45 | 0.8 vhist; .74 vcAMP | 50% @ 17.5 μM | -42% @ 20 |
| 46 | .15 vhist; .36 vcAMP | 50% @ 33 μM | -46% @ 20 |
| 47 | .14 vhist; .10 vcAMP | 50% @ 15 μM | -90% @ 20 |

What is claimed is:

1. A compound of the formula

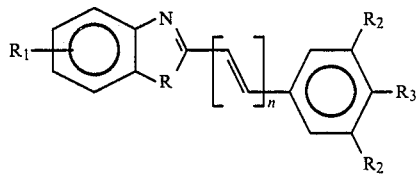

where
R is O
$R_1$ is H, $C_1$-$C_4$ alkyl, $C_1$-$C_4$ alkoxy, Br, Cl or I,
$R_2$ and $R_3$ are H or —O—$(CH_2)_m$—$NR_4R_5$, wherein one of $R_2$ and $R_3$ is H and the other is —O—$(CH_2)_m$—$NR_4R_5$, when $R_3$ is —O—$(CH_2)_m$—$NR_4R_5$, $R_2$ independently is hydrogen, halogen, $C_1$-$C_4$ alkyl or $C_1$-$C_4$ alkoxy,
$R_4$ and $R_5$ are the same or different, and are $C_1$-$C_5$ alkyl, $C_3$-$C_6$ cycloalkyl, benzyl, benzyl substituted by $C_1$-$C_4$ alkyl, $C_1$-$C_4$ alkoxy, Br, Cl, I, or $R_4$ and $R_5$ together with N are piperidine, pyrrolidine, imidazole or N-substituted piperazine, wherein the substituent is $C_1$-$C_4$ alkyl, phenyl or phenyl substituted by $C_1$-$C_3$ alkoxy,
n is 0 or 1, and
m is 2-6,
with the provisos that when m is 2, $R_4$ and $R_5$ cannot both be $C_1$-$C_5$ alkyl and when m is 3, $R_4$ and $R_5$ cannot both be $C_1$-$C_2$ alkyl, and acid addition salts thereof.

2. A compound of claim 1 wherein $R_2$ is H.
3. A compound of claim 1 wherein $R_3$ is H.
4. A compound of claim 1 wherein R is O and $R_1$ is H.
5. A compound of claim 1 selected from the group consisting of (E)-2-[2-(3-dibutylaminopropoxyphenyl)ethenyl]benzoxazole; (E)-2-[2-[3-[3-(4-methylpiperazino)propoxy]phenyl]ethenyl]benzoxazole; (E)-2-[2-(3-dipropylaminopropoxyphenyl)ethenyl]benzoxazole; (E)-2-[2-(3-(1H-imidazol-1-yl)propoxyphenyl)ethenyl]benzoxazole; (E)-2-[2-(3-dipropylaminobutoxyphenyl)ethenyl]benzoxazole; (E)-2-[2-(3-(1H-imidazol-1-yl)butoxyphenyl)ethenyl]benzoxazole; and (E)-2-[2-(3-(1H-imidazol-1-yl)butoxyphenyl)ethenyl]-6-methoxybenzoxazole and acid addition salts thereof.

6. A compound of claim 1 selected from the group consisting of (E)-2-[2-(4-dibutylaminopropoxyphenyl)ethenyl]benzoxazole; (E)-2-[2-(4-dipropylaminopropoxyphenyl)ethenyl]]benzoxazole; (E)-2-[2-(4-(1H-imidazol-1-yl)propoxyphenyl)ethenyl]benzoxazole; (E)-2-[2-(4-diethylaminopropoxyphenyl)ethenyl]benzoxazole; (E)-2-[2-[4-(3-Piperidinopropoxy)phenyl]ethenyl]benzoxazole; (E)-2-[2-[4-(3-methylbenzylaminopropoxy)phenyl]ethenyl]benzoxazole; (E)-2-[2-[4-(2-methoxyphenyl)piperazinopropoxyphenyl]ethenyl]benzoxazole; (E)-2-[2-(4-dibutylaminopropoxyphenyl)ethenyl]-5-methylbenzoxazole; (E)-2-[2-(4-dibutylaminopropoxyphenyl)ethenyl]-6-methoxybenzoxazole; (E)-2-[2-(4-dibutylaminoethoxyphenyl)ethenyl]benzoxazole; (E)-2-[2-(4-dibutylaminobutoxyphenyl)ethenyl]benzoxazole; (E)-2-[2-(4-piperidinobutoxyphenyl)ethenyl]benzoxazole; (E)-2-[2-(4-dipropylaminobutoxyphenyl)ethenyl]benzoxazole; (E)-2-[2-(4-(1H-imidazol-1-yl)butoxyphenyl)ethenyl]benzoxazole; (E)-2-[2-(4-diethylaminobutoxyphenyl)ethenyl]benzoxazole; (E)-2-[2-(4-pyrrolidinobutoxyphenyl)ethenyl]benzoxazole; and (E)-2-[2-(4-(1H-imidazol-1-yl)pentoxyphenyl)ethenyl]benzoxazole and acid addition salts thereof.

7. A compound of claim 1 selected from the group consisting of (E)-2-[2-(3-chloro-4-dipropylaminobutoxyphenyl)ethenyl]benzoxazole, (E)-2-[2-(3,5-dimethoxy-4-dipropylaminopropoxyphenyl)ethenyl]benzoxazole and (E)-2-[2-(3,5-dimethyl-4-dipropylaminopropoxyphenyl)ethenyl]benzoxazole and acid addition salts thereof.

* * * * *